United States Patent [19]

Vanderspurt

[11] 4,248,803
[45] Feb. 3, 1981

[54] OLEFIN OXIDATION CATALYST

[75] Inventor: Thomas H. Vanderspurt, Homestead Park, N.J.

[73] Assignee: Celanese Corporation, New York, N.Y.

[21] Appl. No.: 76,937

[22] Filed: Sep. 19, 1979

Related U.S. Application Data

[62] Division of Ser. No. 960,202, Nov. 13, 1978.

[51] Int. Cl.³ .............................................. C07C 45/34
[52] U.S. Cl. ..................................................... 568/477
[58] Field of Search ................................... 260/604 R

[56] References Cited

U.S. PATENT DOCUMENTS

| | | | |
|---|---|---|---|
| 3,454,630 | 7/1969 | Yamaguchi et al. | 260/604 R |
| 3,546,136 | 12/1970 | Eden | 260/604 R |
| 3,579,574 | 5/1971 | Tenis van der Meer | 260/604 R |
| 3,600,443 | 8/1971 | Cevidalli et al. | 260/604 R |
| 3,778,386 | 12/1973 | Takenaka et al. | 260/604 R |
| 3,825,502 | 7/1974 | Takenaka et al. | 260/604 R |
| 4,001,317 | 1/1977 | Grasselli et al. | 260/604 R |
| 4,035,418 | 7/1977 | Okada et al. | 260/604 R |

*Primary Examiner*—Werren B. Lone
*Attorney, Agent, or Firm*—George A. Depaoli; Kenneth A. Genoni

[57] ABSTRACT

This invention provides an improved catalyst for vapor phase oxidation of propylene or isobutylene to the corresponding acrolein or methacrolein product. In a preferred embodiment, the oxidation catalyst corresponds to the formula:

$$Mo_{12}Ni_6Bi_{1.5-2.5}Co_2Fe_2Sb_2Zn_{0.3-0.8}K_{0.4-2}O_x$$

This invention further provides a method of preparing the improved oxidation catalyst which in one important aspect of the preparation involves controlling the pH of an aqueous slurry admixture of catalyst components within the range of about 1-5.

11 Claims, No Drawings

OLEFIN OXIDATION CATALYST

This is a division of application Ser. No. 960,202, filed Nov. 13, 1978.

BACKGROUND OF THE INVENTION

Various oxidation catalysts have been proposed for use in a vapor phase catalytic oxidation of olefinically unsaturated hydrocarbons to produce corresponding unsaturated aldehydes with a view of enhancing selectivity for desired unsaturated hydrocarbon without reducing conversion of olefin raw material. The known oxidation catalysts include, for example, cuprous oxide, cupric oxide, bismuth molybdate or bismuth phosphomolybdate, cobalt molybdate, antimony oxide, bismuth oxide, vanadium oxide and the like.

U.S. Pat. No. 3,454,630 describes a process for converting propylene and isobutylene to the corresponding unsaturated aldehydes and carboxylic acids in the presence of a catalyst of the elements of Ni, Co, Fe, Bi, P, Mo, O. In U.S. Pat. No. 3,454,630 propylene is oxidized to acrolein in a maximum single pass yield of 71 percent. In Canadian Pat. No. 781,513 the maximum single pass yield of acrolein from propylene is 75.5 percent in the presence of a Ni, Co, Fe, As, Mo, O catalyst.

U.S. Pat. No. 3,778,386 describes a vapor phase oxidation process in which propylene can be converted to acrolein in a single pass yield up to 88 percent.

$$\text{Single pass yield} = \frac{\text{moles of acrolein}}{\text{moles of propylene supplied}} \times 100$$

The U.S. Pat. No. 3,778,386 catalyst contained the following elements on a suitable carrier or binder:

$$Ni_aCo_bFe_cBi_dL_eM_hMo_fO_g$$

where Ni, Co, Fe, Bi, Mo and O are the elements nickel, cobalt, iron, bismuth, molybdenum and oxygen, respectively; L is phosphorous, arsenic or boron, including mixtures; and M is potassium, rubidium or cesium, including mixtures; and where a and b are 0 to 15, while a plus b is 2 to 15, c is 0.5 to 7, d is 0.1 to 4, e is 0 to 4, f is 12, g is 35 to 85 and h is 0.01 to 0.5.

U.S. Pat. No. 4,001,317 describes a process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula:

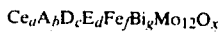

$$Ce_aA_bD_cE_dFe_fBi_gMo_{12}O_x$$

where A is an alkali metal, Tl or a mixture thereof; D is Ni, Co, Mg, Zn, Cd, Ca, Sr or mixture thereof; E is P, As, B, S, Al or mixture thereof; and where a is greater than 0 but less than 5; b and d are 0-4; c, f and g are 0.1-12; and x is the number of oxygens required to satisfy the valence requirements of the other elements present.

U.S. Pat. No. 4,035,418 describes the preparation of a catalyst having the formula:

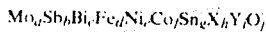

$$Mo_aSb_bBi_cFe_dNi_eCo_fSn_gX_hY_iO_j$$

where a to j represent the atomic ratio of each component and a is 12, b is 0.2 to 20, c is 0.2 to 12, d is 0.2 to 12, e is 0.2 to 12, f is 0 to 20, g is 0 to 20, h is 0.01 to 4, i is 0.01 to 4 and j is a value determined by the valences of the elements in the catalyst, and where X is at least one metal selected from the group consisting of potassium, rubidium, cesium and thallium, and Y is at least one metal selected from the group consisting of selenium, tellurium, gallium, vanadium, ruthenium, zinc, niobium, magnesium, chromium, manganese, cadmium and tantalum.

As noted in the above described prior art processes, when propylene or isobutylene is catalytically oxidized into acrolein or methacrolein in the vapor phase, substantial amounts of byproducts are formed such as carbon monoxide, carbon dioxide, saturated aldehydes (e.g., formaldehyde and acetaldehyde) and acids (e.g., acetic acid and acrylic acid). Furthermore, catalysts which promote acceptable conversion yield and selectivity in the vapor phase oxidation of proplyene or isobutylene to acrolein or methacrolein often exhibit a short catalyst life.

Accordingly, it is a main object of this invention to provide an improved process for high single pass conversion of olefins into the corresponding unsaturated aldehyde derivatives.

It is another object of this invention to provide an improved oxidation catalyst for conversion of acrolein or isobutylene to acrolein or methacrolein with a single pass olefin conversion of at least 95 percent and an unsaturated aldehyde product efficiency of at least 70 percent.

It is a further object of this invention to provide a process for preparing a Mo-Ni-Bi-Co-Fe-Sb-Zn-K-O oxidation catalyst which exhibits extended catalytic activity in vapor phase olefin oxidation processes.

Other objects and advantages shall become apparent from the accompanying description and examples.

DESCRIPTION OF THE INVENTION

One or more objects of the present invention are accomplished by the provision of a process for preparing an oxidation catalyst corresponding to the formula:

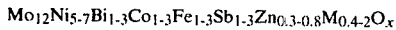

$$Mo_{12}Ni_{5-7}Bi_{1-3}Co_{1-3}Fe_{1-3}Sb_{1-3}Zn_{0.3-0.8}M_{0.4-2}O_x$$

wherein Mo, Ni, Bi, Co, Fe, Sb, Zn, and O are respectively molybdenum, nickel, bismuth, cobalt, iron, antimony, zinc and oxygen; M is at least one element selected from potassium and rubidium; and x represents the number of oxygen atoms between about 35 and 75 sufficient to satisfy the valence requirements of the other elements; said process comprising the steps of (1) admixing and slurrying in an aqueous medium respectively compounds of Mo, Co, Ni, Bi, Sb, Zn and M which are at least partially water-soluble, (2) adjusting the final pH of the aqueous slurry admixture within the range between about 1-5, (3) concentrating the aqueous slurry admixture by water removal to yield a catalyst coprecipitate, (4) heating the catalyst coprecipitate at a temperature in the range between about 200°–250° C. in the presence of molecular oxygen, and (5) calcining the catalyst composition at a temperature between about 400°–600° C. in the presence of molecular oxygen.

More particularly, it has been found that exceptional catalytic reactivity and selectivity for vapor phase oxidation of olefinically unsaturated hydrocarbons to the corresponding olefinically unsaturated aldehydes is achieved with a preferred type of catalyst composition which corresponds to the formula:

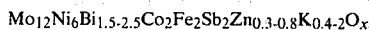

$Mo_{12}Ni_6Bi_{1.5-2.5}Co_2Fe_2Sb_2Zn_{0.3-0.8}K_{0.4-2}O_x$

The preferred type of invention oxidation catalyst is exceptionally effective for close to 100 percent conversion of olefins such as propylene and isobutylene to oxidation products. Further, the said preferred type of present invention oxidation catalyst is highly selective in the conversion of olefins such as propylene and isobutylene to the corresponding aldehydes such as acrolein and methacrolein. Also to be noted as a particularly important characteristic of the preferred oxidation catalyst composition is the ability to catalyze a vapor phase olefin oxidation reaction over an extended catalyst lifetime essentially without loss of catalytic reactivity and selectivity.

Catalyst Preparation

As stated hereinabove, the oxidation catalyst of the present invention has a superior combination of properties which is achieved by a novel method of preparation, which method involves the physical and chemical interaction of specific components in narrowly specific proportions to yield a complex chemical composition of unique structure.

In the invention method of catalyst preparations, compounds of Mo, Sb, Co, Ni, Fe, Zn, Bi, and M are admixed and slurried in an aqueous medium. Normally it is preferred to incorporate in successive order compounds which are water-soluble or at least partially water-soluble to facilitate formation of the ultimate catalyst structure. In a typical preparation an antimony compound is added to an aqueous solution of a molybdate compound such as ammonium molybdate. The antimony compound may be one in which the oxidation state of the Sb is +5, such as $Sb_2O_5$, or it may be one in which the oxidation state of the Sb is +3 or +4. If the Sb oxidation state is less than +5, it is highly preferred that an oxidizing agent such as $H_2O_2$ be employed to oxidize the Sb to the +5 state before the addition of the cobalt, nickel, iron, zinc and bismuth components of the formulation. If the physical properties of the particular catalyst are to be enhanced by the addition of a binder material such as Cab-O-Sil, aerosil or silica sol, at this point in the procedure an appropriate amount is stirred into the aqueous medium.

Then the calculated quantities of compounds of cobalt, nickel, iron, zinc and bismuth are successively added to the catalyst preparation medium, preferably in the form of nitrate salts. The addition is facilitated if each of the nitrate compounds is pre-dissolved in water before the successive addition to the catalyst preparation medium. It is advantageous to pre-dissolve the bismuth salt in dilute nitric acid solution before it is added to the preparation medium. It is to be noted that in the herein described catalyst component addition procedure, the formation of an insoluble precipitate is usually observed upon the addition of the iron nitrate to the catalyst preparation medium.

The successive addition of catalyst components is continued with the addition of a water-soluble compound of the M metal component, such as potassium nitrate or potassium hydroxide.

After the completion of the successive addition of catalyst components, it is essential that the pH of the resultant catalyst preparation medium is in the range between about 1-5, and preferably in the range between about 1.8-3.6. The pH of the catalyst preparation medium can be adjusted by the addition of an acid or base as required, such as by the addition of nitric acid or ammonium hydroxide.

The resultant catalyst preparation medium is concentrated to dryness, such as by spray-drying or by means of a roto-vacuum apparatus. The catalyst precursor solids are recovered and then subjected to a heat treatment at a temperature in the range between about 200°-250° C. in contact with air to effect precalcination of the catalyst precursor mass. The period of heat treatment on the average will be in the range between about 1-24 hours.

The final form of the invention catalyst composition is obtained by calcining the catalyst precursor mixture at a temperature in the range between about 400°-600° C. in the presence of molecular oxygen. The calcination procedure preferably is conducted for a period of time sufficient for the catalyst composition to stabilize in its highest oxidation state, e.g., a calcination period between about 4-20 hours at a temperature in the range of about 450° and 550° C.

The activity of these catalysts is a complex function of calcination procedure, final slurry pH, and M metal (e.g., potassium) level. Calcination at the lower end of the temperature range results in a more active catalyst such as would be more suitable for use with propylene, while calcination at the higher end of the temperature range results in a less active catalyst more suitable for use with isobutylene. Increasing the M metal content decreases the activity. A final slurry pH in the low end of the desired range will result in a catalyst that is more active than one prepared from a final slurry with a pH which is mid-range or above. It is believed that the present invention oxidation catalyst has a complex molybdate phase containing Ni, Sb, Fe, M, and Zn in which are embedded very small crystallites of various phases of $Bi_2O_3$, $Bi_2MoO_6$, $Bi_{20}Mo_8O_{33}$ and $CoMoO_4$. The complex molybdate phase (or phases) is sufficiently disordered to give a very poor PXRD pattern which appears to be similar to the various modifications of $CoMoO_4$.

Catalysts with compositions within the desired range but prepared with a final slurry pH outside that required by the present invention exhibit a PXRD pattern different from catalysts prepared with both proper composition and proper final slurry pH. The most easily noted difference is an excessively high level of $MoO_3$ for those catalysts outside the pH range on the low side. Those outside the pH range on the high side show a great increase in intensity of the strongest $CoMoO_4$ associated reflection and a slight shifting of this line to higher 2θ values.

The physical form of the final catalyst composition can be varied as desired as rough granules, pellets, extrudate, and the like, or coated on the surface of suitable inert spheres or spheroids. These spheres or spheroids most suitable have a rough surface texture and are of silicon carbide, silica, and the like.

Oxidation of Olefins

One or more further objects and advantages of the present invention are accomplished by the provision of a process for the oxidation of olefinically unsaturated hydrocarbons to the corresponding olefinically unsaturated aldehydes which comprises reacting in the vapor phase an olefinically unsaturated hydrocarbon with molecular oxygen in the presence of an oxidation catalyst which corresponds to the formula:

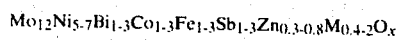

wherein Mo, Ni, Bi, Co, Fe, Sb, Zn and O are respectively the elements of molybdenum, nickel, bismuth, cobalt, iron, antimony, zinc and oxygen; M is at least one element selected from potassium and rubidium; and x represents the number of oxygen atoms between about 35 and 75 sufficient to satisfy the valence requirements of the other elements.

In another preferred embodiment, the present invention provides a process wherein said molecular oxygen is contained in an air stream diluted with a gas selected from steam, nitrogen and carbon dioxide.

The term "olefinically unsaturated hydrocarbons" as employed herein is meant to include alkenes containing between 3 and about 5 carbon atoms as a preferred class of starting materials. It is understood that organic derivatives such as tertiary-butanol or alkyl tertiary-butyl ether (e.g., $C_1$–$C_4$ alkyl such as methyl) may be employed in the vapor phase oxidation process, which derivatives convert to olefinically unsaturated hydrocarbons (e.g., isobutylene) in situ during the oxidation process.

The oxidation process of the present invention utilizing the novel catalysts may be carried out continuously or noncontinuously, and the catalyst may be present in various forms such as in fixed beds or as a fluidized system. Portions of the reactants which do not undergo reaction may be recycled if desired.

The temperatures utilized should generally range between about 200° to 525° C., although the exact temperature utilized in a particular situation will depend largely on the desired product distribution. Thus if it is desired to produce an oxygenated product consisting largely of unsaturated aldehyde with little or no formation of unsaturated acid, then temperatures in the range between about 300° to 400° C. are preferred. However if it is desired to produce a product which contains a minor portion of unsaturated acid in addition to the major portions of unsaturated aldehyde, then higher temperatures in the range of 400° to 525° C. are preferably utilized. The production of mixtures of unsaturated aldehydes and acids are generally most advantageous when the product is to be further oxidized in a second step so as to produce unsaturated acids as the ultimate end product. For example, a two-step process may be utilized for converting propylene to acrylic acid.

The pressure utilized in the process of the present invention may be subatmospheric, atmospheric or superatmospheric but should be between about 0.5 to 3.0 atmospheres for best results, although pressures ranging up to 10 atmospheres may be suitably employed. The contact time for the reactants with the catalyst under the reaction conditions should generally range between about 0.1 to 40 seconds but is preferably a time within the range between about 0.5 and 5 seconds. It has been found that in addition to being dependent on the temperature, the amount of unsaturated acid produced at a given temperature and pressure will increase as the contact time increases. Thus, where it is desired to produce little or no amount of unsaturated acid, the contact time will generally be between 0.1 to 10 seconds, and will usually be between about 4 to 15 seconds when it is desired to produce a product containing a minor portion of unsaturated acid in addition to the unsaturated aldehyde. As used herein the term "contact time" refers to the contact time adjusted to 25° C. and atmospheric pressure. The contact time is calculated by dividing the volume of the catalyst bed (including voids) by the volume per unit time flow rate of the reactants at NTP.

The oxygen source necessary as a reactant in the process may be from concentrated molecular oxygen or may be from a more dilute oxygen-containing gas wherein the molecular oxygen is mixed in varying amounts with an inert diluent gas such as nitrogen, argon or carbon oxides. Preferably, air is utilized as the source of oxygen. The olefinically unsaturated hydrocarbon and/or oxygen-containing gas may be separately introduced into the reaction zone at one or a plurality of points along the length of the reaction zone or may be premixed before entering the reaction zone. However the contact of the olefin and the oxygen-containing charge are preferably kept to a minimum before entering the reaction zone such as for the removal of undesirable components therefrom.

In conducting the oxidation reaction, the gaseous feed mixture should generally contain about 1.0 to 7.0 moles of oxygen per mole of the olefinically unsaturated hydrocarbon, although the preferred range is between about 2.0 and 5 moles per mole. Although it is not required, water in the form of steam is also desirably present in the gaseous feed in amounts of from 0.5 to 15, preferably 2.0 to 15, moles per mole of unsaturated hydrocarbon. In addition to steam, diluents which are gaseous under the reaction conditions and are relatively inert may be introduced into the system. Suitable diluents include carbon dioxide, nitrogen and flue gas, as well as paraffinic hydrocarbons such as are frequently present in commercially-available propylene and isobutylene (e.g., mixtures of propane and propylene obtained from cracking units).

In accordance with the present invention process for oxidizing propylene or isobutylene to acrolein or methacrolein, a single pass conversion of 95 percent of the olefinically unsaturated hydrocarbon feed stream is readily achieved. Further, a single pass conversion efficiency (i.e., selectivity of propylene and isobutylene to acrolein or methacrolein is at least 70 percent under the preferred vapor phase processing conditions described above. Also of importance for the purposes of a two-step commercial operation, in which the present invention process represents the first stage, is the ability of the said invention process to provide a single pass yield of acrolein/acrylic acid or methacrolein/methacrylic acid of at least 70 percent at a space time yield (STY) of at least 250–350 grams per liter per hour.

The following examples are further illustrative of the present invention. The reactants and other specific ingredients are presented as being typical, and various modifications can be devised in view of the foregoing disclosure within the scope of the invention.

EXAMPLE I

Preparation Of
$Mo_{12}Ni_6Bi_2Co_2Fe_2Sb_2Zn_{0.5}K_{0.5}O_x/SiO_2$ As A Selective Oxidation Catalyst To 88.28 grams of $(NH_4)_6Mo_7O_{24} \cdot 4H_2O$ in 200 milliliters of water were added 13.48 grams of $Sb_2O_5$ dispersed in 70 milliliters of water, followed by the additional 55 grams of Nalco 40% $SiO_2$ (type 2327). The pH of the mixture was 6.0. Then 24.23 grams of $Co(NO_3)_2 \cdot 6H_2O$ and 72.70 grams of $Ni(NO_3)_2 \cdot 6H_2O$ were dissolved in 100 milliliters of water and added to the above mixture. The brown slurry which formed had a pH of 6.0.

A 36.67 gram quantity of Fe(NO$_3$)$_3$.9H$_2$O in 100 milliliters of water was added to the above described mixture and the resultant slurry had a pH of 3.0. This was followed by the addition of 6.20 grams of Zn(NO$_3$)$_2$.6H$_2$O in 30 milliliters of water to the above slurry. The slurry pH was now 1.5. Subsequently a solution of 40.4 grams of Bi(NO$_3$)$_3$.5H$_2$O dissolved in 50 milliliters of 10% HNO$_3$ was added, followed by the addition of 2.11 grams of KNO$_3$ in 50 milliliters of water. The resultant slurry pH of 0.0 was adjusted with NH$_4$OH to 3.0 and the slurry stirred at 80° C. for 60 hours.

The slurry was subjected to 5 minutes of efficient blending and then concentrated in a rotary evaporator for 16 hours at 120° C. under 0.5 atmospheric pressure. The coprecipitate mixture of catalyst precursor solids was precalcined at 225° C. for 2 hours, and then calcined at 540° C. for 4 hours in oxygen. The resulting catalyst composition was crushed and sieved to yield 20-30 mesh catalyst particles. About 15 cm$^3$ of the catalyst composition were charged into a 0.-37 inch I.D. reactor tube. A gaseous blend of isobutylene, steam and air was passed through the reactor tube under the processing conditions indicated below.

It has been observed that the properties of the final catalyst composition are affected by the particular sequence of the successive additive of catalyst components to the catalyst preparation medium.

The most preferred catalyst preparation sequence appears to be in the order of (1) the combination of molybdenum compound with an antimony compound (either in the +5 state, or oxidized after addition), and optionally, some or all of the potassium compound (or equivalent element); (2) the addition of binder substrate material; (3) the addition of cobalt and nickel compounds; (4) the addition of iron compound, then bismuth compound; and (5) which is followed by the addition of potassium compound (or equivalent element) if not previously incorporated, and the adjustment of pH into the 1–5 range.

As an alternative catalyst preparation sequence of component addition, a solution containing cobalt, nickel, iron, bismuth and potassium (or equivalent element) compounds can be added to a solution containing molybdenum and antimony (+5). For reasons that are not readily apparent, a catalyst with a less desirable combination of properties is obtained if the solution of molybdenum and antimony compounds is added to the solution of cobalt, nickel, iron, bismuth and potassium compounds, rather than vice versa.

TABLE I

86% (Mo$_{12}$Ni$_6$Bi$_2$Co$_2$Fe$_2$Sb$_2$Zn$_{.5}$K$_{.5}$O$_x$) + 14% SiO$_2$

| Feed, iC$_4$= | mole % Steam | Temp. °C. Bath | Temp. °C. Peak | Contact Time Sec. | iC$_4$= Conv. % | MA Eff. % | MA + MAA Yld % | STY g/l-hr |
|---|---|---|---|---|---|---|---|---|
| 3.2 | 36.9 | 379 | 445 | .74 | 92.8 | 72.2 | 69.4 | 393 |
| 3.2 | 36.8 | 378 | 443 | .74 | 93.3 | 71.5 | 67.5 | 368 |
| 3.0 | 36.7 | 368 | 403 | 1.19 | 92.9 | 73.5 | 69.9 | 267 |
| 3.1 | 36.7 | 367 | 401 | 1.19 | 92.9 | 74.6 | 70.9 | 270 |

EXAMPLE II

Preparation Of Mo$_{12}$Ni$_6$Bi$_2$Co$_2$Fe$_2$Sb$_2$Zn$_{0.5}$K$_1$O$_x$/SiO$_2$ As A Selective Oxidation Catalyst This preparation was conducted in the same manner as Example I except that an antimony +3 compound was employed and it was oxidized to +5 before adding the Co, Ni, Fe, Bi, Zn and K components.

To 88.28 grams of (NH$_4$)$_6$Mo$_7$O$_{24}$.4H$_2$O in 200 milliliters of water were added 12.15 grams of Sb$_2$O$_3$ dispersed in 90 milliliters of H$_2$O, followed by the addition of 55 grams of Nalco 40% SiO$_2$ (type 2327). A 100 milliliter quantity of fresh 30% H$_2$O$_2$ was then added cautiously to the rapidly stirred slurry, and the resultant mixture was refluxed for 16 hours. The pH of the mixture was 6.0. Then 24.25 grams of 6(NO$_3$)$_2$.6H$_2$O and 72.70 grams of Ni(NO$_3$)$_2$.6H$_2$O were dissolved in 100 milliliters of water and added to the above mixture. The brown slurry which resulted had a pH of 6.0.

A 36.37 gram quantity of Fe(NO$_3$)$_3$.9H$_2$O in 100 milliliters of water was added to the above described mixture and the resultant slurry had a pH of 3.0. This was followed by the addition of 6.20 grams of Zn(NO$_3$)$_2$.6H$_2$O in 30 milliliters of water to the above slurry. The slurry pH was now 1.5. Subsequently a solution of 40.4 grams of Bi(NO$_3$)$_3$.5H$_2$O dissolved in 50 milliliters of 10% HNO$_3$ was added, followed by the addition of 4.2 grams of KNO$_3$ in 50 milliliters of water. The resultant slurry pH of 0.0 was adjusted with NH$_4$OH to 3.0, and the slurry was stirred at 80° C. for 16 hours.

The slurry was subjected to 5 minutes of efficient blending, and then concentrated in a rotary evaporator for 16 hours at 120° C. under 0.5 atmospheric pressure. The coprecipitate mixture of catalyst precursor solids was precalcined at 225° C. for 2 hours, and then calcined at 540° C. for 4 hours in oxygen. The resulting catalyst composition was crushed and sieved to yield 20-30 mesh catalyst particles.

About 15 cm$^3$ of the catalyst compostion were charged into a 0.337 inch I.D. reactor tube. A gaseous blend of isobutylene, steam and air was passed through the reactor tube under the processing conditions indicated below.

TABLE II

86% (Mo$_{12}$Ni$_6$Bi$_2$Co$_2$Fe$_2$Sb$_2$Zn$_{.5}$K$_{1.0}$O$_x$) + 14% SiO$_2$

| Feed, iC$_4$= | mole % Steam | Temp. °C. Bath | Temp. °C. Peak | Contact Time Sec. | iC$_4$= Conv. % | MA Eff. % | MA + MAA Yld % | STY g/l-hr |
|---|---|---|---|---|---|---|---|---|
| 2.7 | 35.8 | 373 | 420 | .73 | 92.7 | 73.3 | 69.4 | 330 |
| 2.7 | 35.7 | 373 | 420 | .73 | 93.5 | 75.7 | 72.0 | 364 |
| 2.94 | 37.3 | 373 | 427 | .77 | 93.5 | 75.1 | 71.9 | 380 |
| 2.94 | 37.3 | 373 | 427 | .76 | 96.5 | 74.0 | 73.4 | 367 |
| 2.94 | 37.3 | 373 | 427 | .76 | 96.4 | 72.9 | 72.2 | 354 |

EXAMPLE III

Preparation Of Mo$_{12}$Ni$_6$Bi$_2$Co$_2$Fe$_2$Sb$_2$Zn$_{0.5}$Cs$_{0.5}$O$_x$/SiO$_2$ Oxidation Catalyst This Example illustrates that the substitution of cesium for the potassium component yields an oxidation catalyst not in accordance with the present invention which has inferior conversion and selectivity properties in comparison with the present invention catalyst of Example I.

In this Example the preparation procedure was the same as in Example I, with the exception that 6.4 grams of 50% aqueous CsOH solution was substituted for the KNO$_3$.

TABLE III

84% (Mo$_{12}$Ni$_6$Bi$_2$Co$_2$Fe$_2$Sb$_2$Zn$_{0.5}$Co$_{0.5}$O$_x$) + 14% SiO$_2$

| Feed. iC$_4$= | mole % Steam | Temp. °C. Bath | Temp. °C. Peak | Contact Time Sec. | iC$_4$= Conv. % | MA Eff. % | MA + MAA Yld % | STY g/l-hr |
|---|---|---|---|---|---|---|---|---|
| 2.7 | 38.5 | 407 | 430 | 1.6 | 89 | 63 | 58 | 137 |
| 2.7 | 38.5 | 407 | 430 | 1.6 | 86 | 72 | 61 | 123 |
| 2.7 | 38.5 | 407 | 430 | 1.6 | 86 | 67 | 60 | 134 |
| 2.7 | 38.5 | 414 | 437 | 1.6 | 88 | 65 | 59 | 128 |

EXAMPLE IV

Preparation Of Mo$_{12}$Ni$_6$Bi$_2$Co$_2$Fe$_2$Sb$_2$Zn$_1$K$_1$O$_x$/SiO$_2$ Oxidation Catalyst This Example illustrates that an oxidation catalyst with inferior selectivity properties is obtained when the content of the zinc component is not within the range required for a present invention catalyst.

In this Example the preparation procedure was the same as that in Example II, with the exceptions that 26 grams of (CH$_3$CO$_2$)$_3$Sb were substituted for the Sb$_2$O$_3$ and the quantity of Zn(NO$_3$)$_2$.6H$_2$O was doubled to 12.4 grams (i.e., Zn$_1$, which is not within the present invention Zn$_{0.3-0.8}$ atomic ratio). The final slurry pH was adjusted to 3.0.

TABLE IV

84% (Mo$_{12}$Ni$_6$Bi$_2$Co$_2$Fe$_2$Sb$_2$Zn$_1$K$_1$O$_x$) + 16% SiO$_2$

| Feed. iC$_4$= | mole % Steam | Temp. °C. Bath | Temp. °C. Peak | Contact Time Sec. | iC$_4$= Conv. % | MA Eff. % | MA + MAA Yld % | STY g/l-hr |
|---|---|---|---|---|---|---|---|---|
| 3.0 | 36.3 | 369 | 401 | 1.17 | 92.2 | 58.6 | 54.0 | 192 |

What is claimed is:

1. A process for the oxidation of olefinically unsaturated hydrocarbons to the corresponding olefinically unsaturated aldehydes which comprises reacting in the vapor phase an olefinically unsaturated hydrocarbon with molecular oxygen in the presence of an oxidation catalyst which corresponds to the formula:

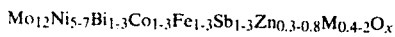
Mo$_{12}$Ni$_{5-7}$Bi$_{1-3}$Co$_{1-3}$Fe$_{1-3}$Sb$_{1-3}$Zn$_{0.3-0.8}$M$_{0.4-2}$O$_x$ wherein Mo, Ni, Bi, Co, Fe, Sb, Zn and O are respectively the elements of molybdenum, nickel, bismuth, cobalt, iron, antimony, zinc and oxygen; M is at least one element selected from potassium and rubidium; and x represents the number of oxygen atoms between about 35 and 75 sufficient to satisfy the valence requirements of the other elements; wherein the said oxidation catalyst is prepared by a process which comprises the steps of (1) admixing and slurrying in an aqueous medium respectively compounds of Mo, Ni, Bi, Co, Fe, Sb, Zn and M which are at least partially water-soluble, (2) adjusting the final pH of the aqueous slurry admixture within the range between about 1-5, (3) concentrating the aqueous slurry admixture by water removal to yield a catalyst coprecipitate, (4) heating the catalyst coprecipitate at a temperature in the range between about 200°-250° C. in the presence of molecular oxygen, and (5) calcining the catalyst composition at a temperature between about 400°-600° C. in the presence of molecular oxygen.

2. A process for producing acrolein or methacrolein which comprises reacting propylene or isobutylene in vapor phase with molecular oxygen at a temperature between about 200°-525° C. in the presence of a catalyst which corresponds to the formula:

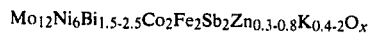
Mo$_{12}$Ni$_6$Bi$_{1.5-2.5}$Co$_2$Fe$_2$Sb$_2$Zn$_{0.3-0.8}$K$_{0.4-2}$O$_x$ wherein Mo, Ni, Bi, Co, Fe, Sb, Zn, K and O are respectively the elements of molybdenum, nickel, bismuth, cobalt, iron, antimony, zinc, potassium and oxygen; and x represents the number of oxygen atoms between about 35 and 75 sufficient to satisfy the valence requirements of the other elements; wherein the said oxidation catalyst is prepared by a process which comprises the steps of (1) admixing and slurrying in an aqueous medium respectively compounds of Mo, Ni, Bi, Co, Fe, Sb, Zn and K which are at least partially water-soluble, (2) adjusting the final pH of the aqueous slurry admixture within the range between about 1-5, (3) concentrating the aqueous slurry admixture by water removal to yield a catalyst coprecipitate, (4) heating the catalyst coprecipitate at a temperature in the range between about 200°-250° C. in the presence of molecular oxygen, and (5) calcining the catalyst composition at a temperature between about 400°-600° C. in the presence of molecular oxygen.

3. A process in accordance with claim 2 wherein the isobutylene is introduced into the vapor phase reaction zone in the form of tertiary-butanol or alkyl tertiary-butyl ether.

4. A process in accordance with claim 2 wherein the molecular oxygen is contained in an air stream.

5. A process in accordance with claim 2 wherein said molecular oxygen is contained in an air stream diluted with a gas selected from steam, nitrogen and carbon dioxide.

6. A process in accordance with claim 2 wherein said molecular oxygen is provided in a mole ratio between about 1.0 and 7 moles per mole of propylene or isobutylene.

7. A process in accordance with claim 2 wherein the temperature in the vapor phase reaction zone is in the range between about 300°-500° C.

8. A process in accordance with claim 2 wherein the contact time between said propylene or isobutylene and molecular oxygen in the vapor phase reaction zone is in the range between about 0.1-40 seconds.

9. A process in accordance with claim 2 wherein the single pass conversion of propylene or isobutylene is at least 95 percent.

10. A process in accordance with claim 2 wherein the single pass conversion efficiency of propylene or isobutylene to acrolein or methacrolein is at least 70 percent.

11. A process in accordance with claim 2 wherein the single pass yield of acrolein/acrylic acid or methacrolein/methacrylic acid is at least 70 percent at a space time yield (STY) of at least 250-350 grams per liter per hour.

* * * * *